(12) United States Patent
Ademovic et al.

(10) Patent No.: US 7,465,709 B2
(45) Date of Patent: Dec. 16, 2008

(54) STRUCTURAL FORMULAS BASED ON THE REPETITIVE MOTIFS OF SALIVARY PROLINE RICH PROTEINS MUCIN AND COLLAGEN DESIGNED TO MODULATE CELL AND TISSUE GROWTH DIVISION AND DIFFERENTIATION

(76) Inventors: Zlatko Ademovic, Titova 17, 76290 Odzak (BA); Nikola Stambuk, Subiceva 16, 10 000 Zagreb (HR); Pasko Konjevoda, Stjepana Draganica 1, 10 000 Zagreb (HR); Darko Mikus, Kukuljeviceva 10, 21 000 Split (HR)

( * ) Notice: Subject to any disclaimer, the term of this patent is extended or adjusted under 35 U.S.C. 154(b) by 464 days.

(21) Appl. No.: 10/492,909

(22) PCT Filed: Nov. 29, 2001

(86) PCT No.: PCT/BA01/00006
§ 371 (c)(1),
(2), (4) Date: Apr. 16, 2004

(87) PCT Pub. No.: WO03/033011
PCT Pub. Date: Apr. 24, 2003

(65) Prior Publication Data
US 2004/0259782 A1 Dec. 23, 2004

(30) Foreign Application Priority Data
Oct. 18, 2001 (BA) .............................. BAP01899A

(51) Int. Cl.
*A61K 38/08* (2006.01)
(52) U.S. Cl. ........................................ 514/16; 530/329
(58) Field of Classification Search .................. None
See application file for complete search history.

(56) References Cited

U.S. PATENT DOCUMENTS 5,981,720 A * 11/1999 Azen et al. ................... 530/412

OTHER PUBLICATIONS

Sanada, 1980, Dep. Oral Biochem., Nippon Dent. Univ., Niigata, 101(5), 251-4 (only 2 pages of Abstract has been provided.)*
Apostolopoulos et al. (1994). Cellular Mucins: Targets for Immunotherapy. Critical Reviews in Immunology 14: 293-309.
Azen et al. (1984). Clones from the Human Gene Complex Coding for Salivary Proline-Rich Proteins. Proc. Natl. Acad. Sci. USA 81: 5561-65.
Baranyi et al. (1995). The antisense homology box: A new motif within proteins that encodes biologically active peptides. Nature Medicine 1: 894-901.
Blalock (1995). Genetic Origins of protein shapes and interactions rules. Nature Medicine 1: 876-878.
Bobek et al. (1993). Molecular Cloning, Sequence, and Specificity of Expression of the Gene Encoding the Low Molecular Weight Human Salivary Mucin (MUC7). J. Biol. Chem. 268: 20563-69.
Chu et al. (1984). Human proα1 (I) Collagen Gene Structure Reveals Evolutionary Conservation of a Pattern of Introns and Exons. Nature 310: 337-40.
Jonsson et al. (2001). Gln-Gly Cleavage: Correlation between Collision-Induced Dissociation and Biological Degradation. J. Am. Soc. Mass Spectrom. 12: 337-42.
Lin et al. (1991). Molecular Characterization of Rat Multigene Family Encoding Proline-Rich Proteins. Genomics 10: 102-13.
Lin et al. (1991). Sequence and Expression of the MnP4 Gene Encoding Basic Proline-Rich Protein in Macaque Salivary Glands. Gene 104: 219-26.
Maeda et al. (1985). Differential RNA Splicing and Post-Translational Cleavages in the Human Salivary-Proline-Rich Protein Gene System. J. Biol. Chem. 260: 11123-30.
Mathison et al. (1994). Neuroendocrine Regulation of Inflammation and Tissue Repair by Submandibular Gland Factors. Immunology Today 15: 527-32.
MathSoft (1999). S-Plus 2000 Guide to Statistics, vol. 2, Data Analysis Products Division, MatchSoft, Seattle, Chapter 4, 67-114.
Naganagowda et al. (1999). NMR Analysis of Human Salivary Mucin (MUC7) Derived O-Linked Model Glycopeptides: Comparison of Structural Features and Carbohydrate-Peptide Interactions. J. Peptide Research 54: 290-310.
Prockop et al. (1995). Collagens: Molecular Biology, Disease, and Potentials for Therapy. Ann. Rev. Biochem. 74: 403-34.
Rose et al. (1985). Hydrophobicity of Amino Acid Residues in Globular Proteins. Science 229: 834-38.
Štambuk et al. (1998). Simple Three-step Method for the Analysis and Design of Repetitive and Bioactive protein Motifs, in: V. B. Bajić (Ed.), Advances in Systems Signals Control and Computers vol. II, IAAMSAD, and ANS, Durban, pp. 310-311.
Štambuk et al. (1999). Computational Determination of biologically active motifs of the bone morphogentic protein precursors. Period. Biol. 101: 363-68.
Štambuk N. (1998). On the Optimization of Complementary Protein Coding, in: S. Ohno, K. Aoki, M. Usui, E. Uchio (Eds.), Uveitis Today, Elsevier, Amsterdam, pp. 315-318.

* cited by examiner

*Primary Examiner*—Andrew D Kosar
*Assistant Examiner*—Satyanarayana Gudibande
(74) *Attorney, Agent, or Firm*—Morgan Lewis & Bockius LLP

(57) ABSTRACT

Computational analysis was used to derive structural peptide formulas SALIVAR, SALIVAL, SALIVAN characterizing common repetitive fragments that reconstruct a large number of salivary proline rich proteins. Short repetitive sequences and variants of the mucin (MUKOSEPT) and collagen (PROCOL α) have been also derived. The purpose of the derived sequences is the modulation of cell and tissue growth, division and differentiation.

14 Claims, 1 Drawing Sheet

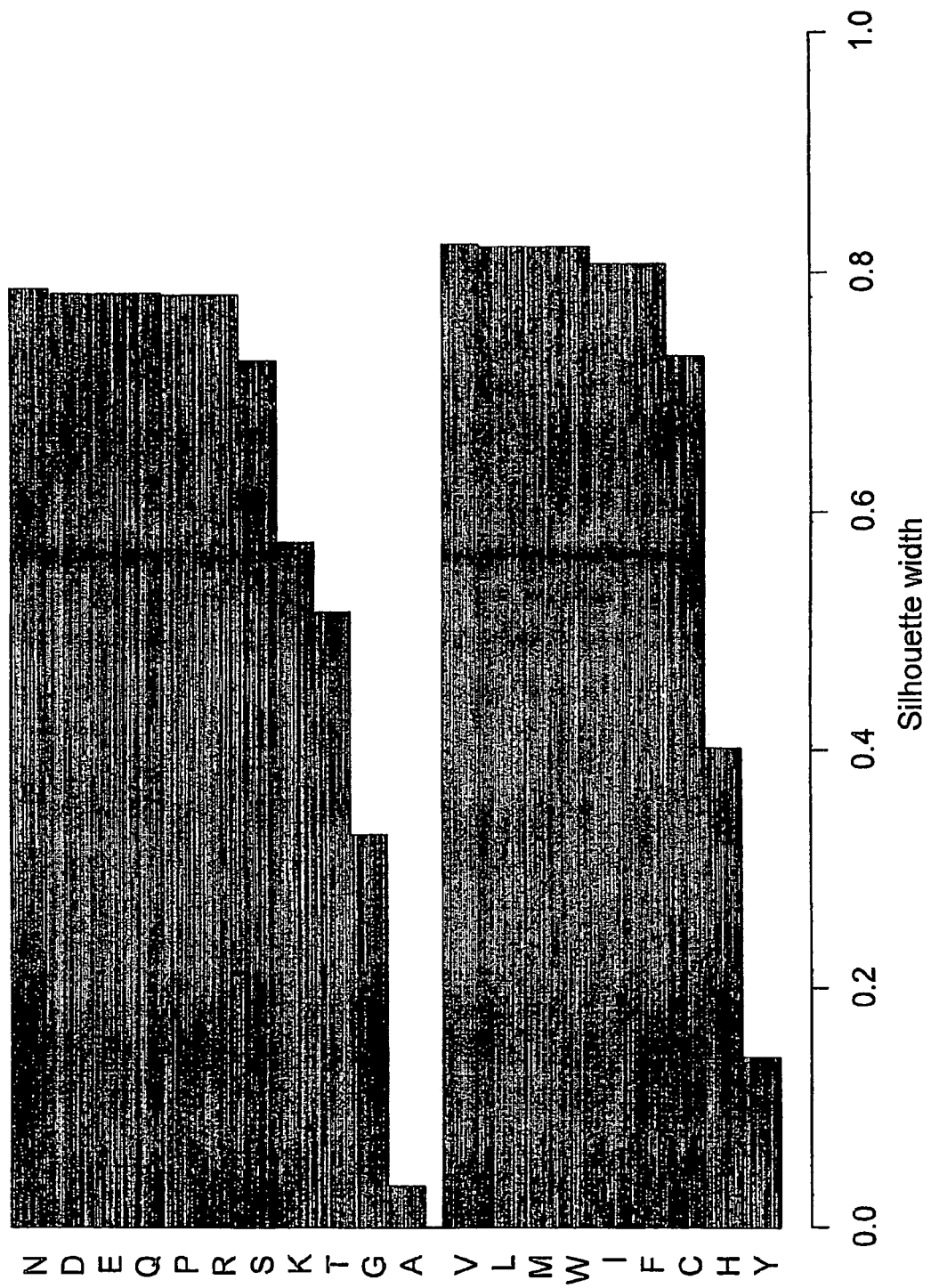

STRUCTURAL FORMULAS BASED ON THE REPETITIVE MOTIFS OF SALIVARY PROLINE RICH PROTEINS MUCIN AND COLLAGEN DESIGNED TO MODULATE CELL AND TISSUE GROWTH DIVISION AND DIFFERENTIATION

1) TECHNICAL AREA OF THE INVENTION

The invention represents five structural chemical formulas of the repetitive sequences (motifs) of the salivary proline rich proteins, mucin and collagen. Peptide sequences are designed for the modulation of cell and tissue growth, division and differentiation.

2) TECHNICAL PROBLEM

Bioactive parts of the protein and gene sequences are often 5 to 15 amino acid long and repetitive peptides, separated by the larger amino acid blocks of undefined function (1-5). Computational analyses may be used for the extraction of such motifs and subsequent manipulation with the bioactive effects their protein regions (1-5). The invention represents five structural formulas for the repetitive sequences (motifs) of the salivary proline rich proteins, mucin and collagen.

3) TECHNICAL DESCRIPTION

Repetitive peptide motifs within a single protein or a protein family represent, together with their matching complementary sequences, regions that are linked to the bioactivity of the larger molecular structures (1-5).

Modern programming techniques, development of the softwares and large databases of the protein and gene structures, enabled the computer modelling of repetitive, bioactive and complementary structures of the large number of different proteins (1-5). Consequently, the extraction of short and repetitive motifs may be done on a personal computer quickly and easily (1-5). We analysed repetitive peptides of the salivary proline rich proteins, mucin and collagen (6-9) by means of the software SCAN (3-5) in order to define five structural peptide formulas (SALIVAR, SALIVAL, SALIVAN, MUCOSEPT and PROCOL α) to modulate cell and tissue growth, division and differentiation.

4) PURPOSE OF THE INVENTION

The invention consists of five peptide structural formulas from the repetitive parts of the salivary proline rich proteins, mucin and type I collagen. The aim of the invention, i.e. structural formulas, is to provide short peptide sequences that modulate cell and tissue growth, division and differentiation.

The technical invention is in the fact that the sequences that model large and/or bioactive parts of the molecules of the salivary proline rich proteins, mucin and type I collagen are extracted by means of the software SCAN, instead of the random pharmacological screening. Based on the computational analyses and database search general structural formulas (motifs) have been derived as the consensus sequences salivary proline rich proteins, mucin and collagen.

5) BRIEF DESCRIPTION OF DRAWINGS

Table 1 defines repetitive peptide sequence (motif) SALIVAR.

Table 2 defines general repetitive peptide sequence (motif) SALIVAR.

Table 3 defines repetitive peptide sequence (motif) SALIVAL.

Table 4 defines general repetitive peptide sequence (motif) SALIVAL.

Table 5 defines specific peptide sequences (motifs) SALIVAL.

Table 6 defines repetitive peptide sequence (motif) SALIVAN.

Table 7 defines repetitive peptide sequence (motif) MUCOSEPT.

Table 8 defines repetitive peptide sequence (motif) PROCOL α.

Table 9 defines general and specific peptide sequences (motifs) PROCOL α.

FIG. 1 describes the partition of the amino acids according to the molecular polarity, in the sequences of the Tables 4, 5, 8 and 9.

6) DESCRIPTION OF THE POSSIBLE APPLICATIONS OF THE INVENTION

Repetitive sequences SALIVAR, SALIVAL, SALIVAN, MUCOSEPT and PROCOL α, defined in Tables 1-9 will be used as bioactive peptides for the modulation of cell and tissue growth, division and differentiation. The purpose of defining repetitive segments SALIVAR, SALIVAL and SALIVAN of the bioactive salivary proline rich proteins (8) is to obtain quickly and accurately the formula (sequence motif) that in the satisfactory way mimics the function of larger structures. Additional bioactivity of the motifs is to be obtained by combining the sequences SALIVAR, SALIVAL and SALIVAN with the repetitive sequences of their mucin or collagen matrix (MUCOSEPT, PROCOL α).

7) INDUSTRIAL APPLICATIONS OF THE INVENTION

Bioactive sequences of the formulas (motifs) SALIVAR, SALIVAL, SALIVAN, MUCOSEPT and PROCOL α, and their combination will be applied perorally, intramuscularly and intravenously. Topical applications include ointments, creams, gels, suppositories, vaginal suppositories, eye-drops and ear-drops.

REFERENCES

1. L. Baranyi, W. Campbell, K. Ohishima et al., *Nature Medicine* 1 (1995) 894-901.
2. J. E. Blalock, *Nature Medicine*, 1 (1995) 876-878.
3. N. Stambuk, *On the Optimization of Complementary Protein Coding*, in: S. Ohno, K. Aoki, M. Usui, E. Uchio (Eds.), *Uveitis Today*, Elsevier, Amsterdam, 1998, pp 315-318.
4. N. Stambuk and P. Konjevoda, *Period. Biol.* 101 (1999) 363-368.
5. N. Stambuk, N. Gotovac, M. Martinis et al. Simple Three-step Method for the Analysis and Design of Repetitive and Bioactive protein Motifs, in: V. B. Bajić (Ed.), Advances in Systems Signals Control and Computers vol. II, IAAM-SAD, and ANS, Durban, 1998, pp 310-311.
6. A. Gougos, and M. Letarte, *J. Biol. Chem.* 265 (1990) 8361-8364.
7. H. Kuivaniemi, G. Tromp and D. J. Prockop, *Human Mutation* 9 (1997) 300-315.
8. R. Mathison, J. S. Davison and A. D. Befus, *Immunol Today* 15 (1994) 527-532.
9. R. Mehrotra, D. J. Thornton and J. K. Sheehan, *Biochem J.* 334 (1998) 415-422.
10. G. D. Rose, A. R. Geselowitz, G. J. Lesser et al., *Science* 229 (1985) 834-838.
11. MathSoft. S-PLUS 2000 Guide to Statistics, Volume 2, Data Analysis Products Division, MathSoft, Seattle, 1999, Chapter 4.

TABLE 1

Octapeptide GKPQGPPP (SEQ ID NO: 1) derived by means of the SCAN software
(3-5) represents the common building block of a large number of salivary proline
rich proteins is patented under the name SALIVAR.

Database: nr

Category: Eukaryota

Sequence: GKPQGPPP (SEQ ID NO: 1)

gi|88462|pir||A27307 PROLINE-RICH PHOSPHOPROTEIN (GENE PRH1, DB

ALLELE) - HUMAN Matching:PPPPPGKPQGPPPQGGRP (Residues 149-156) (SEQ ID NO: 28)

gi|88466|pir||B25372 SALIVARY PROLINE-RICH PHOSPHOPROTEIN PRECURSOR

PRH1 (ALLELE PIF) - HUMAN Matching:PPPPPGKPQGPPPQGGRP (Residues 144-151) (SEQ ID NO: 29)

gi|105417|pir||D38355 BASIC PROLINE-RICH PEPTIDE IB-8A - HUMAN (FRAGMENTS) Matching:SPPGKPQGPPPQGGNQ (Residues 4-11) (SEQ ID NO: 30)

PPPPPGKPQGPPPQGGNK (Residues 25-32) (SEQ ID NO: 31)

GPPPPGKPQGPPPQGDNK (Residues 45-52) (SEQ ID NO: 32)

PPPQGGKPQGPPPQGGNK (Residues 71-78) (SEQ ID NO: 33)

gi|105420|pir||C38355 BASIC PROLINE-RICH PEPTIDE II-2 - HUMAN

Matching:PPPPPGKPQGPPPQGGNK (Residues 40-47) (SEQ ID NO: 34)

GPPPPGKPQGPPPQGDKS (Residues 60-67) (SEQ ID NO: 35)

gi|107422|pir||B36298 PROLINE-RICH PROTEIN PRB3S (CYS) - HUMAN (FRAGMENT) Matching:PPPHPGKPQGPPPQEGNK (Residues 147-154) (SEQ ID NO: 36)

LPPPAGKPQGPPPPPQGG (Residues 188-195) (SEQ ID NO: 37)

gi|4826938|ref|NP_005030.1| PROLINE-RICH PROTEIN BSTNI SUBFAMILY 1

Matching:PPPPPGKPQGPPPQGGNK (Residues 55-62) (SEQ ID NO: 38)

GPPPPGKPQGPPPQGDKS (Residues 75-82) (SEQ ID NO: 39)

PRSPPGKPQGPPPQGGNQ (Residues 95-102) (SEQ ID NO: 40)

PPPPPGKPQGPPPQGGNK (Residues 116-123) (SEQ ID NO: 41)

GPPPPGKPQGPPPQGDKS (Residues 136-143) (SEQ ID NO: 42)

PRSPPGKPQGPPPQGGNQ (Residues 156-163) (SEQ ID NO: 43)

GPPPPGKPQGPPPQGDKS (Residues 197-204) (SEQ ID NO: 44)

PQSPPGKPQGPPPQGGNQ (Residues 217-224) (SEQ ID NO: 45)

PPPPPGKPQGPPPQGGNK (Residues 238-245) (SEQ ID NO: 46)

gi|130998|sp|P02812|PRP2_HUMAN SALIVARY PROLINE-RICH PROTEIN

PRECURSOR (CLONE CP7) [CONTAINS: BASIC PEPTIDE P-F]

Matching:SRSPPGKPQGPPPQGGNQ (Residues 13-20) (SEQ ID NO: 47)

PPPPPGKPQGPPPQGGNK (Residues 34-41) (SEQ ID NO: 48)

GPPPPGKPQGPPPQGDNK (Residues 54-61) (SEQ ID NO: 49)

ARSPPGKPQGPPPQGGNQ (Residues 75-82) (SEQ ID NO: 50)

PPPPPGKPQGPPPQGDNK (Residues 96-103) (SEQ ID NO: 51)

GPPPPGKPQGPPPQGGSK (Residues 116-123) (SEQ ID NO: 52)

SRSPPGKPQGPPPQGGNQ (Residues 137-144) (SEQ ID NO: 53)

PPPPPGKPQGPPPQGGNK (Residues 158-165) (SEQ ID NO: 54)

TABLE 1-continued

Octapeptide GKPQGPPP (SEQ ID NO: 1) derived by means of the SCAN software
(3-5) represents the common building block of a large number of salivary proline
rich proteins is patented under the name SALIVAR.

GPPPPGKPQGPPPQGGSK (Residues 178-185) (SEQ ID NO: 55)

gi|4506037|ref|NP_002714.1| PROLINE-RICH PROTEIN BSTNI SUBFAMILY 4

Matching:PPPPPGKPQGPPPQGGNQ (Residues 55-62) (SEQ ID NO: 56)

GPPPPGKPQGPPPAGGNP (Residues 201-208) (SEQ ID NO: 57)

QDPPAGKPQGPPPPPQGG (Residues 222-229) (SEQ ID NO: 58)

gi|131006|sp|P04281|PRP5_HUMAN BASIC PROLINE-RICH PEPTIDE IB-1

Matching:PPSPPGKPQGPPPQGGNQ (Residues 39-46) (SEQ ID NO: 59)

PPPPPGKPQGPPPQGGNK (Residues 60-67) (SEQ ID NO: 60)

GPPPPGKPQGPPPQGDKS (Residues 80-87) (SEQ ID NO: 61)

gi|131008|sp|P02810|PRPC_HUMAN SALIVARY ACIDIC PROLINE-RICH

PHOSPHOPROTEIN 1/2 PRECURSOR (PRP-1/PRP-3) (PRP-2/PRP-4)

(PIF-F/PIF-S) (PROTEIN A/PROTEIN C) [CONTAINS: PEPTIDE P-C]

Matching:PPPPPGKPQGPPPQGGRP (Residues 144-151) (SEQ ID NO: 62)

gi|131009|sp|P02811|PRPE_HUMAN BASIC PROLINE-RICH PEPTIDE P-E (IB-9)

Matching:SPPGKPQGPPPQGGNQ (Residues 4-11) (SEQ ID NO: 63)

PPPPPGKPQGPPPQGGNR (Residues 25-32) (SEQ ID NO: 64)

GPPPPGKPQGPPPQGDKS (Residues 45-52) (SEQ ID NO: 65)

gi|131011|sp|P10162|PRPL_HUMAN SALIVARY PROLINE-RICH PROTEIN PO (ALLELE K) [CONTAINS: PEPTIDE P-D] Matching:PPPPPGKPQGPPPQGGNQ (Residues 21-28) (SEQ ID NO: 66)

GPPPPGKPQGPPPPGGNP (Residues 230-237) (SEQ ID NO: 67)

QAPPAGKPQGPPPPPQGG (Residues 251-258) (SEQ ID NO: 68)

gi|190474|gb|AAA36502.1| (K02576) SALIVARY PROLINE-RICH PROTEIN 1

[HOMO SAPIENS] Matching:PPPPPGKPQGPPPQGGNK (Residues 38-45) (SEQ ID NO: 69)

GPPPPGKPQGPPPQGGKR (Residues 58-65) (SEQ ID NO: 70)

PRSPPGKPQGPPPQGGNQ (Residues 79-86) (SEQ ID NO: 71)

PPPPPGKPQGPPPQGGNK (Residues 100-107) (SEQ ID NO: 72)

GPPPPGKPQGPPPQGDKS (Residues 120-127) (SEQ ID NO: 73)

gi|4826944|ref|NP_005033.1| PROLINE-RICH PROTEIN HAEIII SUBFAMILY 2

Matching:PPPPPGKPQGPPPQGGRP (Residues 144-151) (SEQ ID NO: 74)

gi|190504|gb|AAA60186.1| (K03205) SALIVARY PROLINE-RICH PROTEIN

PRECURSOR [HOMO SAPIENS] Matching:PPPPPGKPQGPPPQGGNK (Residues 55-62) (SEQ ID NO: 75)

GPPPPGKPQGPPPQGDKS (Residues 75-82) (SEQ ID NO: 760)

PRSPPGKPQGPPPQGGKP (Residues 95-102) (SEQ ID NO: 77)

PPPQGGKPQGPPPQGGNK (Residues 105-112) (SEQ ID NO: 78)

gi|190506|gb|AAA60187.1| (K03206) SALIVARY PROLINE-RICH PROTEIN

TABLE 1-continued

Octapeptide GKPQGPPP (SEQ ID NO: 1) derived by means of the SCAN software
(3-5) represents the common building block of a large number of salivary proline
rich proteins is patented under the name SALIVAR.

PRECURSOR [HOMO SAPIENS] Matching:PPPPPGKPQGPPPQGGNK (Residues 55-62) (SEQ ID NO: 79)

GPPPPGKPQGPPPQGDKS (Residues 75-82) (SEQ ID NO: 80)

PRSPPGKPQGPPPQGGKP (Residues 95-102) (SEQ ID NO: 81)

gi|7427521|ref|NP_006240.2| PROLINE-RICH PROTEIN BSTNI SUBFAMILY 3

Matching:PPPHPGKPQGPPPQEGNK (Residues 244-251) (SEQ ID NO: 82)

LPPPAGKPQGPPPPPQGG (Residues 285-292) (SEQ ID NO: 83)

gi|296670|emb|CAA30729.1| (X07882) PO PROTEIN [HOMO SAPIENS]

Matching:LFLISGKPQGPPPQGGNQ (Residues 34-41) (SEQ ID NO: 84)

GPPPPGKPQGPPPAGGNP (Residues 180-187) (SEQ ID NO: 85)

QAPPAGKPQGPPPPPQGG (Residues 201-208) (SEQ ID NO: 86)

gi|350322|prf||0605215A PEPTIDE PC,SALIVARY PRO RICH [HOMO SAPIENS]

Matching:PPPPPGKPQGPPPQGGRP (Residues 22-29) (SEQ ID NO: 87)

gi|351207|prf||0903209A PEPTIDE PD,BASIC PRO RICH [HOMO SAPIENS]

Matching:GPPPPGKPQGPPPPGGNP (Residues 24-31) (SEQ ID NO: 88)

QAPPAGKPQGPPPPPQGG (Residues 45-52) (SEQ ID NO: 89)

gi|351237|prf||0904270A PEPTIDE PF,BASID PRO RICH [HOMO SAPIENS]

Matching:SPPGKPQGPPPQGGNQ (Residues 4-11) (SEQ ID NO: 90)

PPPPPGKPQGPPPQGGNK (Residues 25-32) (SEQ ID NO: 91)

GPPPPGKPQGPPPQGGSK (Residues 45-52) (SEQ ID NO: 92)

gi|386431|gb|AAB27288.1| (S62928) PRB1M PRECURSOR PROTEIN = BASIC

PROLINE-RICH PROTEINS (PS, PMF, PMS, AND PE) PRECURSOR(PS 1 = BASIC

PROLINE-RICH PROTEIN) {C-TERMINAL} [HUMAN, SALIVARY, PEPTIDE

PARTIAL, 297 AA] [HOMO SAPIENS] Matching:PPPPPGKPQGPPPQGGNK (Residues 21- 28) (SEQ ID NO: 93)

GPPPPGKPQGPPPQGDKS (Residues 41-48) (SEQ ID NO: 94)

PRSPPGKPQGPPPQGGNQ (Residues 61-68) (SEQ ID NO: 95)

PPPPPGKPQGPPPQGGNK (Residues 82-89) (SEQ ID NO: 96)

GPPPPGKPQGPPPQGDKS (Residues 102-109) (SEQ ID NO: 97)

PRSPPGKPQGPPPQGGNQ (Residues 122-129) (SEQ ID NO: 98)

GPPPPGKPQGPPPQGDKS (Residues 163-170) (SEQ ID NO: 99)

PQSPPGKPQGPPPQGGNQ (Residues 183-190) (SEQ ID NO: 100)

PPPPPGKPQGPPPQGGNK (Residues 204-211) (SEQ ID NO: 101)

gi|386433|gb|AAB27289.1| (S62941) PS 2 = BASIC PROLINE-RICH

PROTEIN(PRB1L PRECURSOR PROTEIN = BASIC PROLINE-RICH PROTEINS (PS,

PMF, PMS, AND PE) PRECURSOR) {C-TERMINAL} [HUMAN, SALIVARY, PEPTIDE

PARTIAL, 358 AA] [HOMO SAPIENS] Matching:PPPPPGKPQGPPPQGGNK (Residues 21-28) (SEQ ID NO: 102)

TABLE 1-continued

Octapeptide GKPQGPPP (SEQ ID NO: 1) derived by means of the SCAN software (3-5) represents the common building block of a large number of salivary proline rich proteins is patented under the name SALIVAR.

GPPPPGKPQGPPPQGDKS (Residues 41-48) (SEQ ID NO: 103)

PRSPPGKPQGPPPQGGNQ (Residues 61-68) (SEQ ID NO: 104)

PPPPPGKPQGPPPQGGNK (Residues 82-89) (SEQ ID NO: 105)

GPPPPGKPQGPPPQGDKS (Residues 102-109) (SEQ ID NO: 106)

PRSPPGKPQGPPPQGGNQ (Residues 122-129) (SEQ ID NO: 107)

PPPPPGKPQGPPPQGGNK (Residues 143-150) (SEQ ID NO: 108)

GPPPPGKPQGPPPQGDKS (Residues 163-170) (SEQ ID NO: 109)

PRSPPGKPQGPPPQGGNQ (Residues 183-190) (SEQ ID NO: 110)

GPPPPGKPQGPPPQGDKS (Residues 224-231) (SEQ ID NO: 111)

PQSPPGKPQGPPPQGGNQ (Residues 244-251) (SEQ ID NO: 112)

PPPPPGKPQGPPPQGGNK (Residues 265-272) (SEQ ID NO: 113)

GPPPPGKPQGPPPQGGSK (Residues 285-292) (SEQ ID NO: 114)

gi|3914451|sp|P81489|PRPP_HUMAN SALIVARY PROLINE-RICH PROTEIN II-1

Matching:PPPPPGKPQGPPPQGGDQ (Residues 38-45) (SEQ ID NO: 115)

gi|433011|gb|AAB27290.1| (S62929) PRB1L PRECURSOR PROTEIN = BASIC PROLINE RICH PROTEINS (PS, PMF, PMS, AND PE) PRECURSOR {C-TERMINAL} [HUMAN, SALIVARY, PEPTIDE PARTIALMUTANT, 358 AA] [HOMO SAPIENS]

Matching:PPPPPGKPQGPPPQGGNK (Residues 21-28) (SEQ ID NO: 116)

GPPPPGKPQGPPPQGDKS (Residues 41-48) (SEQ ID NO: 117)

PRSPPGKPQGPPPQGGNQ (Residues 61-68) (SEQ ID NO: 118)

PPPPPGKPQGPPPQGGNR (Residues 82-89) (SEQ ID NO: 119)

GPPPPGKPQGPPPQGDKS (Residues 102-109) (SEQ ID NO: 120)

PXSPPGKPQGPPPQGGNQ (Residues 122-129) (SEQ ID NO: 121)

PPPPPGKPQGPPPQGGKK (Residues 143-150) (SEQ ID NO: 122)

GPPPPGKPQGPPPQGDKS (Residues 163-170) (SEQ ID NO: 123)

PRSPPGKPQGPPPQGGNQ (Residues 183-190) (SEQ ID NO: 124)

GPPPPGKPQGPPPQGDKS (Residues 224-231) (SEQ ID NO: 125)

SQSPPGKPQGPPPQGGNQ (Residues 244-251) (SEQ ID NO: 126)

PPPPPGKPQGPPPQGGNK (Residues 265-272) (SEQ ID NO: 127)

gi|433012|gb|AAB27291.1| (S62936) PRB1S PRECURSOR PROTEIN = BASIC PROLINE-RICH PROTEINS (PS, PMF, PMS, AND PE) PRECURSOR {C-TERMINAL} [HUMAN, SALIVARY, PEPTIDE PARTIALMUTANT, 236 AA] [HOMO SAPIENS]

Matching:PPPPPGKPQGPPPQGGNK (Residues 21-28) (SEQ ID NO: 128)

GPPPPGKPQGPPPQGDKS (Residues 41-48) (SEQ ID NO: 129)

PRSPPGKPQGPPPQGGNQ (Residues 61-68) (SEQ ID NO: 130)

PPSPPGKPQGPPPQGGNR (Residues 82-89) (SEQ ID NO: 131)

GPPPPGKPQGPPPQGDKS (Residues 102-109) (SEQ ID NO: 132)

TABLE 1-continued

Octapeptide GKPQGPPP (SEQ ID NO: 1) derived by means of the SCAN software
(3-5) represents the common building block of a large number of salivary proline
rich proteins is patented under the name SALIVAR.

PXSPPGKPQGPPPQGGNQ (Residues 122-129) (SEQ ID NO: 133)

PPPPPGKPQGPPPQGGNK (Residues 143-150) (SEQ ID NO: 134)

gi|539667|pir||D40750 PROLINE-RICH PROTEIN PRB1/2S (EA) - HUMAN (FRAGMENT) Matching:PPPPPGKPQGPPPQGGNK (Residues 21-28) (SEQ ID NO: 135)

GPPPPGKPQGPPPQGDKS (Residues 41-48) (SEQ ID NO: 136)

PRSPPGKPQGPPPQGGNQ (Residues 61-68) (SEQ ID NO: 137)

PPSPPGKPQGPPPQGGNR (Residues 82-89) (SEQ ID NO: 138)

GPPPPGKPQGPPPQGDKS (Residues 102-109) (SEQ ID NO: 139)

gi|1709793|sp|P10161|PRPM_HUMAN SALIVARY PROLINE-RICH PROTEIN PO (ALLELE M) [CONTAINS: PEPTIDE P-D] Matching:PPPPPGKPQGPPPQGGNQ (Residues 21-28) (SEQ ID NO: 140)

GPPPPGKPQGPPPPGGNP (Residues 188-195) (SEQ ID NO: 141)

QAPPAGKPQGPPPPPQGG (Residues 209-216) (SEQ ID NO: 142)

gi|1911490|gb|AAB50686.1| (S80905) CON1 = SALIVARY CONCANAVALIN-A

BINDING PROTEIN {EXON 3} [HUMAN, PERIPHERAL BLOOD LEUKOCYTES,

SUBJECT "R.S.", PEPTIDE PARTIAL MUTANT, 382 AA] [HOMO SAPIENS]

Matching:PPSPPGKPQGPPPQGGNQ (Residues 21-28) (SEQ ID NO: 143)

PPPPPGKPQGPPPQGGNK (Residues 42-49) (SEQ ID NO: 144)

GPPPPGKPQGPPPQGDKS (Residues 62-69) (SEQ ID NO: 145)

PRSPPGKPQGPPPQGGNQ (Residues 82-89) (SEQ ID NO: 146)

PPPPPGKPQGPPPQGGNK (Residues 103-110) (SEQ ID NO: 147)

GPPPPGKPQGPPPQGDNK (Residues 123-130) (SEQ ID NO: 148)

SRSPPGKPQGPPPQGGNQ (Residues 144-151) (SEQ ID NO: 149)

PPPPPGKPQGPPPQGGNK (Residues 165-172) (SEQ ID NO: 150)

GPPPPGKPQGPPPQGDNK (Residues 185-192) (SEQ ID NO: 151)

ARSPPGKPQGPPPQGGNQ (Residues 206-213) (SEQ ID NO: 152)

PPPPPGKPQGPPPQGGNK (Residues 227-234) (SEQ ID NO: 153)

GPPPPGKPQGPPPQGGSK (Residues 247-254) (SEQ ID NO: 154)

SRSPPGKPQGPPPQGGNQ (Residues 268-275) (SEQ ID NO: 155)

PPPPPGKPQGPPPQGGNK (Residues 289-296) (SEQ ID NO: 156)

GPPPPGKPQGPPPQGGSK (Residues 309-316) (SEQ ID NO: 157)

gi|1911492|gb|AAB50687.1| (S80916) PAROTID "O" PROTEIN, PO = SALIVARY

PROLINE-RICH PROTEIN {EXON 3} [HUMAN, PERIPHERAL BLOOD LEUKOCYTES,

SUBJECT "J.J.", PEPTIDE PARTIAL MUTANT, 234 AA] [HOMO SAPIENS]

Matching:PPPPPGKPQGPPPQGGNQ (Residues 21-28) (SEQ ID NO: 158)

GPPPPGKPQGPPPPGGNP (Residues 188-195) (SEQ ID NO: 159)

QAPPAGKPQGPPPPPQGG (Residues 209-216) (SEQ ID NO: 160)

gi|2144910|pir||PIHUB6 SALIVARY PROLINE-RICH PROTEIN PRECURSOR PRB1

TABLE 1-continued

Octapeptide GKPQGPPP (SEQ ID NO: 1) derived by means of the SCAN software
(3-5) represents the common building block of a large number of salivary proline
rich proteins is patented under the name SALIVAR.

(LARGE ALLELE) - HUMAN Matching:PPPPPGKPQGPPPQGGNK (Residues 55-62) (SEQ ID NO: 161)

GPPPPGKPQGPPPQGDKS (Residues 75-82) (SEQ ID NO: 162)

PRSPPGKPQGPPPQGGNQ (Residues 95-102) (SEQ ID NO: 163)

PPPPPGKPQGPPPQGGNK (Residues 116-123) (SEQ ID NO: 164)

GPPPPGKPQGPPPQGDKS (Residues 136-143) (SEQ ID NO: 165)

PRSPPGKPQGPPPQGGNQ (Residues 156-163) (SEQ ID NO: 166)

PPPPPGKPQGPPPQGGNK (Residues 177-184) (SEQ ID NO: 167)

GPPPPGKPQGPPPQGDKS (Residues 197-204) (SEQ ID NO: 168)

PRSPPGKPQGPPPQGGNQ (Residues 217-224) (SEQ ID NO: 169)

GPPPPGKPQGPPPQGDKS (Residues 258-265) (SEQ ID NO: 170)

PQSPPGKPQGPPPQGGNQ (Residues 278-285) (SEQ ID NO: 171)

PPPPPGKPQGPPPQGGNK (Residues 299-306) (SEQ ID NO: 172)

gi|2144912|pir||PIHUSD SALIVARY PROLINE-RICH GLYCOPROTEIN PRECURSOR

PRB4 (LARGE ALLELE) - HUMAN Matching:PPPPPGKPQGPPPQGGNQ (Residues 55-62) (SEQ ID NO: 173)

GPPPPGKPQGPPPPGGNP (Residues 264-271) (SEQ ID NO: 174)

QAPPAGKPQGPPPPPQGG (Residues 285-292) (SEQ ID NO: 175)

gi|91204|pir||A29149 PROLINE-RICH PROTEIN - MOUSE

Matching:KPPQPGKPQGPPPPGGPQ (Residues 66-73) (SEQ ID NO: 176)

KPPQSGKPQGPPPPGGPQ (Residues 104-111) (SEQ ID NO: 177)

gi|131003|sp|P04474|PRP3_RAT ACIDIC PROLINE-RICH PROTEIN PRP33

PRECURSOR Matching:RPPQPGKPQGPPPQGGPQ (Residues 148-155) (SEQ ID NO: 178)

gi|131000|sp|P10164|PRP2_RAT ACIDIC PROLINE-RICH PROTEIN PRP25

PRECURSOR Matching:KPPQPGKPQGPPPPGGPQ (Residues 85-92) (SEQ ID NO: 179)

KPPQPGKPQGPPPPGGPQ (Residues 104-111) (SEQ ID NO: 180)

KPPQAGKPQGPPPPGGPQ (Residues 142-149) (SEQ ID NO: 181)

gi|6981414|ref|NP_036764.1| PROLINE-RICH PROTEIN, SALIVARY

Matching:KPPQPGKPQGPPPPGGPQ (Residues 64-71) (SEQ ID NO: 182)

KPPQPGKPQGPPPPGGPQ (Residues 83-90) (SEQ ID NO: 183)

KPPQSGKPQGPPPPGGPQ (Residues 121-128) (SEQ ID NO: 184)

gi|112206|pir||A39066 PROLINE-RICH PROTEIN 4 - RAT

Matching:KPPQPGKPQGPPPPGGPQ (Residues 104-111) (SEQ ID NO: 185)

KPPQPGKPQGPPPPGGPQ (Residues 142-149) (SEQ ID NO: 186)

KPPQPGKPQGPPPPGGPQ (Residues 161-168) (SEQ ID NO: 187)

gi|206716|gb|AAA42066.1| (M64791) SALIVARY PROLINE-RICH PROTEIN

[*RATTUS NORVEGICUS*] Matching:KPPQPGKPQGPPPPGGPQ (Residues 159-

TABLE 1-continued

Octapeptide GKPQGPPP (SEQ ID NO: 1) derived by means of the SCAN software
(3-5) represents the common building block of a large number of salivary proline
rich proteins is patented under the name SALIVAR.

166) (SEQ ID NO: 188)

gi|1083763|pir||A48013 PROLINE-RICH PROTEOGLYCAN 1 PRECURSOR,

PAROTID - RAT Matching:TSPQPGKPQGPPPQGGPQ (Residues 111-118) (SEQ ID NO: 189)

gi|2119707|pir||A42817 PROLINE-RICH PROTEIN PRECURSOR - RAT

Matching:KPPQPGKPQGPPPPGGPQ (Residues 85-92) (SEQ ID NO: 190)

KPPQPGKPQGPPPPGGPQ (Residues 104-111) (SEQ ID NO: 191)

KPPQPGKPQGPPPPGGPQ (Residues 123-130) (SEQ ID NO: 192)

KPPQPGKPQGPPPPGGPQ (Residues 142-149) (SEQ ID NO: 193)

KPPQPGKPQGPPPPGGPQ (Residues 180-187) (SEQ ID NO: 194)

TABLE 2

General formula GKPαβPPP (SEQ ID NO: 2) of the repetitive
octapeptide motif SALIVAR computationally defined
in a large number of salivary proline rich proteins by
means of the SCAN software (3-5) on a proteins
available in the nr Database of human protein sequences.
All combinations presented in the table are patented.

|   | α |   |
|---|---|---|
| β | Q | E |
| G | +++ | ++ |
| R | 0 | ++ |
| E | 0 | 1 |

+++ = >15 repetitive motifs in the first 100 proteins
++ = 5-15 repetitive motifs in the first 100 proteins
α = Q, E
β = G, R, E

TABLE 3

Sequence (formula) of the repetitive octapeptide motif GPPPPGKP (SEQ ID NO: 3)
of the salivary proteins is defined by shifting the end of the formula GKPQβPPP in the sliding
block window of the protein for 5 amino acid residues left until the next residue Q, so that the
structural formula GPPPPGKP (SEQ ID NO: 3) remains defined by means of the left and
right residue Q, e.g. QGPPPPGKPQ. This procedure has been tested on a large set of salivary
proteins in the nr Database of human protein sequences, by means of the software SCAN (3-
5). The sequence is patented under the name SALIVAL.

Database: nr

Category: Eukaryota

Sequence: GPPPPGKP (SEQ ID NO: 3)

gi|105417|pir||D38355 BASIC PROLINE-RICH PEPTIDE IB-8A - HUMAN (FRAGMENTS) Matching:GNKPQGPPPPGKPQGPPP (Residues 40-47) (SEQ ID NO: 195)

gi|105420|pir||C38355 BASIC PROLINE-RICH PEPTIDE II-2 - HUMAN

Matching:GNKPQGPPPPGKPQGPPP (Residues 55-62) (SEQ ID NO: 196)

gi|4826938|ref|NP_005030.1| PROLINE-RICH PROTEIN BSTNI SUBFAMILY 1

Matching:GNKPQGPPPPGKPQGPPP (Residues 70-77) (SEQ ID NO: 197)

GNKPQGPPPPGKPQGPPP (Residues 131-138) (SEQ ID NO: 198)

| TABLE 3-continued |
|---|
| Sequence (formula) of the repetitive octapeptide motif GPPPPGKP (SEQ ID NO: 3) of the salivary proteins is defined by shifting the end of the formula GKPQβPPP in the sliding block window of the protein for 5 amino acid residues left until the next residue Q, so that the structural formula GPPPPGKP (SEQ ID NO: 3) remains defined by means of the left and right residue Q, e.g. QGPPPPGKPQ. This procedure has been tested on a large set of salivary proteins in the nr Database of human protein sequences, by means of the software SCAN (3-5). The sequence is patented under the name SALIVAL. |

GNRPQGPPPPGKPQGPPP (Residues 192-199) (SEQ ID NO: 199)

GNKPQGPPPPGKPQGPPA (Residues 253-260) (SEQ ID NO: 200)

gi|130998|sp|P02812|PRP2_HUMAN SALIVARY PROLINE-RICH PROTEIN

PRECURSOR (CLONE CP7) [CONTAINS: BASIC PEPTIDE P-F]

Matching:GNKPQGPPPPGKPQGPPP (Residues 49-56) (SEQ ID NO: 201)

DNKSQGPPPPGKPQGPPP (Residues 111-118) (SEQ ID NO: 202)

GNKPQGPPPPGKPQGPPP (Residues 173-180) (SEQ ID NO: 203)

gi|4506037|ref|NP_002714.1| PROLINE-RICH PROTEIN BSTNI SUBFAMILY 4

Matching:GNKPQGPPPPGKPQGPPP (Residues 196-203) (SEQ ID NO: 204)

gi|131006|sp|P04281|PRP5_HUMAN BASIC PROLINE-RICH PEPTIDE IB-1

Matching:GNKPQGPPPPGKPQGPPP (Residues 75-82) (SEQ ID NO: 205)

gi|131009|sp|P02811|PRPE_HUMAN BASIC PROLINE-RICH PEPTIDE P-E (IB-9)

Matching:GNRPQGPPPPGKPQGPPP (Residues 40-47) (SEQ ID NO: 206)

gi|131011|sp|P10162|PRPL_HUMAN SALIVARY PROLINE-RICH PROTEIN PO (ALLELE K) [CONTAINS: PEPTIDE P-D] Matching:GNKPQGPPPPGKPQGPPP (Residues 225-232) (SEQ ID NO: 207)

gi|190474|gb|AAA36502.1| (K02576) SALIVARY PROLINE-RICH PROTEIN 1

[HOMO SAPIENS] Matching:GNKPQGPPPPGKPQGPPP (Residues 53-60) (SEQ ID NO: 208)

GNKPQGPPPPGKPQGPPP (Residues 115-122) (SEQ ID NO: 209)

gi|190475|gb|AAA36503.1| (K02576) SALIVARY PROLINE-RICH PROTEIN 1

[HOMO SAPIENS] Matching:GNKPQGPPPPGKPQGPPA (Residues 15-22) (SEQ ID NO: 210)

gi|190504|gb|AAA60186.1| (K03205) SALIVARY PROLINE-RICH PROTEIN

PRECURSOR [HOMO SAPIENS] Matching:GNKPQGPPPPGKPQGPPP (Residues 70-77) (SEQ ID NO: 211)

GNKPQGPPPPGKPQGPPA (Residues 120-127) (SEQ ID NO: 212)

gi|190506|gb|AAA60187.1| (K03206) SALIVARY PROLINE-RICH PROTEIN

PRECURSOR [HOMO SAPIENS] Matching:GNKPQGPPPPGKPQGPPP (Residues 70-77) (SEQ ID NO: 213)

gi|296670|emb|CAA30729.1| (X07882) PO PROTEIN [HOMO SAPIENS]

Matching:GNKPQGPPPPGKPQGPPP (Residues 175-182) (SEQ ID NO: 214)

gi|351207|prf||0903209A PEPTIDE PD, BASIC PRO RICH [HOMO SAPIENS]

Matching:GNKPQGPPPPGKPQGPPP (Residues 19-26) (SEQ ID NO: 215)

TABLE 3-continued

Sequence (formula) of the repetitive octapeptide motif GPPPPGKP (SEQ ID NO: 3) of the salivary proteins is defined by shifting the end of the formula GKPQβPPP in the sliding block window of the protein for 5 amino acid residues left until the next residue Q, so that the structural formula GPPPPGKP (SEQ ID NO: 3) remains defined by means of the left and right residue Q, e.g. QGPPPPGKPQ. This procedure has been tested on a large set of salivary proteins in the nr Database of human protein sequences, by means of the software SCAN (3-5). The sequence is patented under the name SALIVAL.

gi|351237|prf||0904270A PEPTIDE PF, BASID PRO RICH [HOMO SAPIENS]

Matching:GNKPQGPPPPGKPQGPPP (Residues 40-47) (SEQ ID NO: 216)

gi|386431|gb|AAB27288.1| (S62928) PRB1M PRECURSOR PROTEIN = BASIC

PROLINE-RICH PROTEINS (PS, PMF, PMS, AND PE) PRECURSOR(PS 1 = BASIC

PROLINE-RICH PROTEIN) {C-TERMINAL} [HUMAN, SALIVARY, PEPTIDE

PARTIAL, 297 AA] [HOMO SAPIENS] Matching:GNKPQGPPPPGKPQGPPP (Residues 36-43) (SEQ ID NO: 217)

GNKPQGPPPPGKPQGPPP (Residues 97-104) (SEQ ID NO: 218)

GNRPQGPPPPGKPQGPPP (Residues 158-165) (SEQ ID NO: 219)

GNKPQGPPPPGKPQGPPA (Residues 219-226) (SEQ ID NO: 220)

gi|386433|gb|AAB27289.1| (S62941) PS 2 = BASIC PROLINE-RICH

PROTEIN(PRB1L PRECURSOR PROTEIN = BASIC PROLINE-RICH PROTEINS (PS,

PMF, PMS, AND PE) PRECURSOR) {C-TERMINAL} [HUMAN, SALIVARY, PEPTIDE

PARTIAL, 358 AA] [HOMO SAPIENS] Matching:GNKPQGPPPPGKPQGPPP (Residues 36-43) (SEQ ID NO: 221)

GNKPQGPPPPGKPQGPPP (Residues 97-104) (SEQ ID NO: 222)

GNKPQGPPPPGKPQGPPP (Residues 158-165) (SEQ ID NO: 223)

GNRPQGPPPPGKPQGPPP (Residues 219-226) (SEQ ID NO: 224)

GNKPQGPPPPGKPQGPPP (Residues 280-287) (SEQ ID NO: 225)

gi|433011|gb|AAB27290.1| (S62929) PRB1L PRECURSOR PROTEN = BASIC

PROLINE RICH PROTEINS (PS, PMF, PMS, AND PE) PRECURSOR {C-TERMINAL}

[HUMAN, SALIVARY, PEPTIDE PARTIALMUTANT, 358 AA] [HOMO SAPIENS]

Matching:GNKPQGPPPPGKPQGPPP (Residues 36-43) (SEQ ID NO: 226)

GNRPQGPPPPGKPQGPPP (Residues 97-104) (SEQ ID NO: 227)

GKKPQGPPPPGKPQGPPP (Residues 158-165) (SEQ ID NO: 228)

GNRPQGPPPPGKPQGPPP (Residues 219-226) (SEQ ID NO: 229)

GNKPQGPPPPGKPQGPPA (Residues 280-287) (SEQ ID NO: 230)

gi|433012|gb|AAB27291.1| (S62936) PRB1S PRECURSOR PROTEIN = BASIC

PROLINE-RICH PROTEINS (PS, PMF, PMS, AND PE) PRECURSOR {C-TERMINAL}

[HUMAN, SALIVARY, PEPTIDE PARTIALMUTANT, 236 AA] [HOMO SAPIENS]

Matching:GNKPQGPPPPGKPQGPPP (Residues 36-43) (SEQ ID NO: 231)

GNRPQGPPPPGKPQGPPP (Residues 97-104) (SEQ ID NO: 232)

GNKPQGPPPPGKPQGPPA (Residues 158-165) (SEQ ID NO: 233)

gi|539667|pir||D40750 PROLINE-RICH PROTEIN PRB1/2S (EA) - HUMAN (FRAGMENT) Matching:GNKPQGPPPPGKPQGPPP (Residues 36-43) (SEQ ID NO: 234)

TABLE 3-continued

Sequence (formula) of the repetitive octapeptide motif GPPPPGKP (SEQ ID NO: 3) of the salivary proteins is defined by shifting the end of the formula GKPQβPPP in the sliding block window of the protein for 5 amino acid residues left until the next residue Q, so that the structural formula GPPPPGKP (SEQ ID NO: 3) remains defined by means of the left and right residue Q, e.g. QGPPPPGKPQ. This procedure has been tested on a large set of salivary proteins in the nr Database of human protein sequences, by means of the software SCAN (3-5). The sequence is patented under the name SALIVAL.

GNRPQGPPPPGKPQGPPP (Residues 97-104) (SEQ ID NO: 235)

gi|1709793|sp|P10161|PRPM_HUMAN SALIVARY PROLINE-RICH PROTEIN PO (ALLELE M) [CONTAINS: PEPTIDE P-D] Matching:GNKPQGPPPPGKPQGPPP (Residues 183-190) (SEQ ID NO: 236)

gi|1911490|gb|AAB50686.1| (S80905) CON1 = SALIVARY CONCANAVALIN-A

BINDING PROTEIN {EXON 3} [HUMAN, PERIPHERAL BLOOD LEUKOCYTES,

SUBJECT "R.S.", PEPTIDE PARTIAL MUTANT, 382 AA] [HOMO SAPIENS]

Matching:GNKPQGPPPPGKPQGPPP (Residues 57-64) (SEQ ID NO: 237)

GNKPQGPPPPGKPQGPPP (Residues 118-125) (SEQ ID NO: 238)

GNKPQGPPPPGKPQGPPP (Residues 180-187) (SEQ ID NO: 239)

GNKSQGPPPPGKPQGPPP (Residues 242-249) (SEQ ID NO: 240)

GNKPQGPPPPGKPQGPPP (Residues 304-311) (SEQ ID NO: 241)

gi|1911492|gb|AAB50687.1| (S80916) PAROTID "O" PROTEIN, PO = SALIVARY

PROLINE-RICH PROTEIN {EXON 3} [HUMAN, PERIPHERAL BLOOD LEUKOCYTES,

SUBJECT "J.J.", PEPTIDE PARTIAL MUTANT, 234 AA] [HOMO SAPIENS]

Matching:GNKPQGPPPPGKPQGPPP (Residues 183-190) (SEQ ID NO: 242)

gi|2144910|pir||PIHUB6 SALIVARY PROLINE-RICH PROTEIN PRECURSOR PRB1

(LARGE ALLELE) - HUMAN Matching:GNKPQGPPPPGKPQGPPP (Residues 70-77) (SEQ ID NO: 243)

GNKPQGPPPPGKPQGPPP (Residues 131-138) (SEQ ID NO: 244)

GNKPQGPPPPGKPQGPPP (Residues 192-199) (SEQ ID NO: 245)

GNRPQGPPPPGKPQGPPP (Residues 253-260) (SEQ ID NO: 246)

GNKPQGPPPPGKPQGPPA (Residues 314-321) (SEQ ID NO: 247)

gi|2144912|pir||PIHUSD SALIVARY PROLINE-RICH GLYCOPROTEIN PRECURSOR

PRB4 (LARGE ALLELE) - HUMAN Matching: GNKPQGPPPPGKPQGPPP (Residues 259-266) (SEQ ID NO: 248)

gi|86621|pir||JH0481 BASIC PROLINE-RICH PROTEIN MNP4 - CRAB-EATING

MACAQUE Matching:GKKPQGPPPPGKPQGPPK (Residues 70-77) (SEQ ID NO: 249)

GKKPQGPPPPGKPQGPPQ (Residues 90-97) (SEQ ID NO: 250)

GNKPQGPPPPGKPQGPPQ (Residues 110-117) (SEQ ID NO: 251)

GNKPQGPPPPGKPQGPPQ (Residues 130-137) (SEQ ID NO: 252)

TABLE 4

General structural formulas (sequences) of the repetitive
octapeptide motif SALIVAL computationally defined in a large
number of salivary proteins present in the nr Database of human
sequences, by means of the SCAN software (3-5). a = polar amino
acid (N, D, E, Q, P, R, S, K, T, G or A), b = non-polar amino acid
(V, L, M, W, I, F, C, H or Y), as defined in the FIG. 1. Sequences
are patented under the name SALIVAL as follows.

| No. | Sequence |
|---|---|
| 1 | bPPPPGK (SEQ ID NO: 4) |
| 2 | aPPPPGK (SEQ ID NO: 5) |
| 3 | PPPPGKb (SEQ ID NO: 6) |
| 4 | PPPPGKa (SEQ ID NO: 7) |
| 5 | bPPPPGKb (SEQ ID NO: 8) |
| 6 | bPPPPGKa (SEQ ID NO: 9) |
| 7 | aPPPPGKb (SEQ ID NO: 10) |
| 8 | aPPPPGKa (SEQ ID NO: 11) |
| 9 | aaPPPGaa (SEQ ID NO: 12) |

TABLE 5

Specific variants of the formula (sequence) of the octapeptide motif SALIVAL defined in the large number of human salivary protein sequences of the nr Database by means of the software SCAN (3-5). Sequences are patented under the name SALIVAL as follows.

| No. Sequence | Protein homology | Residue |
|---|---|---|
| 10 IPPPPGK (SEQ ID NO: 13) | Telomerase associated protein 1 | 865-871 |
| 11 GEPPPGKP (SEQ ID NO:14) | Bone morphogenetic protein 6 precursor | 122-129 |

TABLE 6

Sequence (formula) of the repetitive octapeptide motif GGNaP (SEQ ID NO: 15) of
the salivary proteins is defined by shifting the formula GKPQβPPP (Table 3) in the sliding
block window of the protein sequence for 14 amino acid residues left until the next residue Q,
so that the structural formula GPPPPGKP is defined by means of the left and right residue Q,
e.g. QGPPPPGKPQ. This procedure has been tested on a large set of salivary proteins in the
nr Database of human protein sequences, by means of the software SCAN (3-5). The
sequence is patented under the name SALIVAN.

Database: nr

Category: Eukaryota

Sequence: GGNKP (SEQ ID NO: 16)

gi|105417|pir||D38355 BASIC PROLINE-RICH PEPTIDE IB-8A - HUMAN (FRAGMENTS) Matching:GPPPQGGNKPQGPPPP (Residues 34-39) (SEQ ID NO: 253)

GPPPQGGNKPQGPPPQ (Residues 80-85) (SEQ ID NO: 254)

gi|105420|pir||C38355 BASIC PROLINE-RICH PEPTIDE II-2 - HUMAN

Matching:GPSPQGGNKPQGPPPP (Residues 27-32) (SEQ ID NO: 255)

GPPPQGGNKPQGPPPP (Residues 49-54) (SEQ ID NO: 256)

gi|107421|pir||A36298 PROLINE-RICH PROTEIN PRB3M (NULL) - HUMAN (FRAGMENT) Matching:GPPPQGGNKPQGPPPS (Residues 198-203) (SEQ ID NO: 257)

gi|107422|pir||B36298 PROLINE-RICH PROTEIN PRB3S (CYS) - HUMAN (FRAGMENT) Matching:GSPSQGGNKPQGPPPH (Residues 135-140) (SEQ ID NO: 258)

gi|4826938|ref|NP_005030.1| PROLINE-RICH PROTEIN BSTNI SUBFAMILY 1

Matching:GPSPQGGNKPQGPPPP (Residues 43-48) (SEQ ID NO: 259)

GPPPQGGNKPQGPPPP (Residues 64-69) (SEQ ID NO: 260)

GPPPQGGNKPQGPPPP (Residues 125-130) (SEQ ID NO: 261)

GPPPQGGNKPQGPPPP (Residues 247-252) (SEQ ID NO: 262)

gi|130998|sp|P02812|PRP2_HUMAN SALIVARY PROLINE-RICH PROTEIN

PRECURSOR (CLONE CP7) [CONTAINS: BASIC PEPTIDE P-F]

TABLE 6-continued

Sequence (formula) of the repetitive octapeptide motif GGNaP (SEQ ID NO: 15) of the salivary proteins is defined by shifting the formula GKPQβPPP (Table 3) in the sliding block window of the protein sequence for 14 amino acid residues left until the next residue Q, so that the structural formula GPPPPGKP is defined by means of the left and right residue Q, e.g. QGPPPPGKPQ. This procedure has been tested on a large set of salivary proteins in the nr Database of human protein sequences, by means of the software SCAN (3-5). The sequence is patented under the name SALIVAN.

Matching:GPPPQGGNKPQGPPPP (Residues 43-48) (SEQ ID NO: 263)

GPPPQGGNKPQGPPPP (Residues 167-172) (SEQ ID NO: 264)

gi|131006|sp|P04281|PRP5_HUMAN BASIC PROLINE-RICH PEPTIDE IB-1

Matching:GAPPQGGNKPQGPPSP (Residues 27-32) (SEQ ID NO: 265)

GPPPQGGNKPQGPPPP (Residues 69-74) (SEQ ID NO: 266)

gi|190474|gb|AAA36502.1| (K02576) SALIVARY PROLINE-RICH PROTEIN 1

[HOMO SAPIENS] Matching:GPPPQGGNKPQGPPPP (Residues 26-31) (SEQ ID NO: 267)

GPPPQGGNKPQGPPPP (Residues 47-52) (SEQ ID NO: 268)

GPPPQGGNKPQGPPPP (Residues 109-114) (SEQ ID NO: 269)

gi|190475|gb|AAA36503.1| (K02576) SALIVARY PROLINE-RICH PROTEIN 1

[HOMO SAPIENS] Matching:GPPPTGGNKPQGPPPP (Residues 9-14) (SEQ ID NO: 270)

gi|190504|gb|AAA60186.1| (K03205) SALIVARY PROLINE-RICH PROTEIN

PRECURSOR [HOMO SAPIENS] Matching:GPSPQGGNKPQGPPPP (Residues 43-48) (SEQ ID NO: 271)

GPPPQGGNKPQGPPPP (Residues 64-69) (SEQ ID NO: 272)

GPPPQGGNKPQGPPPP (Residues 114-119) (SEQ ID NO: 273)

gi|190506|gb|AAA60187.1| (K03206) SALIVARY PROLINE-RICH PROTEIN

PRECURSOR [HOMO SAPIENS] Matching:GPSPQGGNKPQGPPPP (Residues 43-48) (SEQ ID NO: 274)

GPPPQGGNKPQGPPPP (Residues 64-69) (SEQ ID NO: 275)

gi|351237|prf||0904270A PEPTIDE PF, BASID PRO RICH [HOMO SAPIENS]

Matching:GPPPQGGNKPQGPPPP (Residues 34-39) (SEQ ID NO: 276)

gi|386431|gb|AAB27288.1| (S62928) PRB1M PRECURSOR PROTEIN = BASIC

PROLINE-RICH PROTEINS (PS, PMF, PMS, AND PE) PRECURSOR(PS 1 = BASIC

PROLINE-RICH PROTEIN) {C-TERMINAL} [HUMAN, SALIVARY, PEPTIDE

PARTIAL, 297 AA] [HOMO SAPIENS] Matching:GPSPQGGNKPQGPPPP (Residues 9-14) (SEQ ID NO: 277)

GPPPQGGNKPQGPPPP (Residues 30-35) (SEQ ID NO: 278)

GPPPQGGNKPQGPPPP (Residues 91-96) (SEQ ID NO: 279)

GPPPQGGNKPQGPPPP (Residues 213-218) (SEQ ID NO: 280)

gi|386433|gb|AAB27289.1| (S62941) PS 2 = BASIC PROLINE-RICH

PROTEIN(PRB1L PRECURSOR PROTEIN = BASIC PROLINE-RICH PROTEINS (PS,

PMF, PMS, AND PE) PRECURSOR) {C-TERMINAL} [HUMAN, SALIVARY, PEPTIDE

PARTIAL, 358 AA] [HOMO SAPIENS] Matching:GPSPQGGNKPQGPPPP (Residues 9-14) (SEQ ID NO: 281)

GPPPQGGNKPQGPPPP (Residues 30-35) (SEQ ID NO: 282)

TABLE 6-continued

Sequence (formula) of the repetitive octapeptide motif GGNaP (SEQ ID NO: 15) of the salivary proteins is defined by shifting the formula GKPQβPPP (Table 3) in the sliding block window of the protein sequence for 14 amino acid residues left until the next residue Q, so that the structural formula GPPPPGKP is defined by means of the left and right residue Q, e.g. QGPPPPGKPQ. This procedure has been tested on a large set of salivary proteins in the nr Database of human protein sequences, by means of the software SCAN (3-5). The sequence is patented under the name SALIVAN.

GPPPQGGNKPQGPPPP (Residues 91-96) (SEQ ID NO: 283)

GPPPQGGNKPQGPPPP (Residues 152-157) (SEQ ID NO: 284)

GPPPQGGNKPQGPPPP (Residues 274-279) (SEQ ID NO: 285)

gi|433011|gb|AAB27290.1| (S62929) PRB1L PRECURSOR PROTEIN = BASIC

PROLINE RICH PROTEINS (PS, PMF, PMS, AND PE) PRECURSOR {C-TERMINAL}

[HUMAN, SALIVARY, PEPTIDE PARTIALMUTANT, 358 AA] [HOMO SAPIENS]

Matching:GPSPQGGNKPQGPPPP (Residues 9-14) (SEQ ID NO: 286)

GPPPQGGNKPQGPPPP (Residues 30-35) (SEQ ID NO: 287)

GPPPQGGNKPQGPPPP (Residues 274-279) (SEQ ID NO: 288)

gi|433012|gb|AAB27291.1| (S62936) PRB1S PRECURSOR PROTEIN = BASIC

PROLINE-RICH PROTEINS (PS, PMF, PMS, AND PE) PRECURSOR {C-TERMINAL}

[HUMAN, SALIVARY, PEPTIDE PARTIALMUTANT, 236 AA] [HOMO SAPIENS]

Matching:GPSPQGGNKPQGPPPP (Residues 9-14) (SEQ ID NO: 289)

GPPPQGGNKPQGPPPP (Residues 30-35) (SEQ ID NO: 290)

GPPPQGGNKPQGPPPP (Residues 152-157) (SEQ ID NO: 291)

gi|539667|pir||D40750 PROLINE-RICH PROTEIN PRB1/2S (EA) - HUMAN (FRAGMENT) Matching:GPSPQGGNKPQGPPPP (Residues 9-14) (SEQ ID NO: 292)

GPPPQGGNKPQGPPPP (Residues 30-35) (SEQ ID NO: 293)

gi|1911490|gb|AAB50686.1| (S80905) CON 1 = SALIVARY CONCANAVALIN-A

BINDING PROTEIN {EXON 3} [HUMAN, PERIPHERAL BLOOD LEUKOCYTES,

SUBJECT "R.S.", PEPTIDE PARTIAL MUTANT, 382 AA] [HOMO SAPIENS]

Matching:GAPPQGGNKPQGPPSP (Residues 9-14) (SEQ ID NO: 294)

GPPPQGGNKPQGPPPP (Residues 51-56) (SEQ ID NO: 295)

GPPPQGGNKPQGPPPP (Residues 112-117) (SEQ ID NO: 296)

GPPPQGGNKPQGPPPP (Residues 174-179) (SEQ ID NO: 297)

GPPPQGGNKPQGPPPP (Residues 298-303) (SEQ ID NO: 298)

gi|2144910|pir||PIHUB6 SALIVARY PROLINE-RICH PROTEIN PRECURSOR PRB1

(LARGE ALLELE) - HUMAN Matching:GPSPQGGNKPQGPPPP (Residues 43-

48) (SEQ ID NO: 299)

GPPPQGGNKPQGPPPP (Residues 64-69) (SEQ ID NO: 300)

GPPPQGGNKPQGPPPP (Residues 125-130) (SEQ ID NO: 301)

GPPPQGGNKPQGPPPP (Residues 186-191) (SEQ ID NO: 302)

GPPPQGGNKPQGPPPP (Residues 308-313) (SEQ ID NO: 303)

gi|7662112|ref|NP_055587.1| KIAA0427 GENE PRODUCT

Matching:QQRPPGGNKPQQHGDH (Residues 202-207) (SEQ ID NO: 304)

TABLE 6-continued

Sequence (formula) of the repetitive octapeptide motif GGNaP (SEQ ID NO: 15) of the salivary proteins is defined by shifting the formula GKPQβPPP (Table 3) in the sliding block window of the protein sequence for 14 amino acid residues left until the next residue Q, so that the structural formula GPPPPGKP is defined by means of the left and right residue Q, e.g. QGPPPPGKPQ. This procedure has been tested on a large set of salivary proteins in the nr Database of human protein sequences, by means of the software SCAN (3-5). The sequence is patented under the name SALIVAN.

gi|86621|pir||JH0481 BASIC PROLINE-RICH PROTEIN MNP4 - CRAB-EATING

MACAQUE Matching:GPPQQGGNKPQGPPPP (Residues 104-109) (SEQ ID NO: 305)

GPPQQGGNKPQGPPPP (Residues 124-129) (SEQ ID NO: 306)

gi|4582086|emb|CAB40256.1| (AJ241213) NADH DEHYDROGENASE SUBUNIT 1

[ECHINOCOCCUS GRANULOSUS] Matching:GGXXXQSFADL (Residues 1-6) (SEQ ID NO: 307)

************************************************************************

Database: nr

Category: Eukaryota

Sequence: GGNRP (SEQ ID NO: 17)

gi|4826938|ref|NP_005030.1| PROLINE-RICH PROTEIN BSTNI SUBFAMILY 1

Matching:GPPQQGGNRPQGPPPP (Residues 186-191) (SEQ ID NO: 308)

gi|131009|sp|P02811|PRPE_HUMAN BASIC PROLINE-RICH PEPTIDE P-E (IB-9)

Matching:GPPPQGGNRPQGPPPP (Residues 34-39) (SEQ ID NO: 309)

gi|386431|gb|AAB27288.1| (S62928) PRB1M PRECURSOR PROTEIN = BASIC

PROLINE-RICH PROTEINS (PS, PMF, PMS, AND PE) PRECURSOR(PS 1 = BASIC

PROLINE-RICH PROTEIN) {C-TERMINAL} [HUMAN, SALIVARY, PEPTIDE

PARTIAL, 297 AA] [HOMO SAPIENS] Matching:GPPQQGGNRPQGPPPP (Residues 152-157) (SEQ ID NO: 310)

gi|386433|gb|AAB27289.1| (S62941) PS 2 = BASIC PROLINE-RICH

PROTEIN(PRB1L PRECURSOR PROTEIN = BASIC PROLINE-RICH PROTEINS (PS,

PMF, PMS, AND PE) PRECURSOR) {C-TERMINAL} [HUMAN, SALIVARY, PEPTIDE

PARTIAL, 358 AA] [HOMO SAPIENS] Matching:GPPQQGGNRPQGPPPP (Residues 213-218) (SEQ ID NO: 311)

gi|433011|gb|AAB27290.1| (S62929) PRB1L PRECURSOR PROTEIN = BASIC

PROLINE RICH PROTEINS (PS, PMF, PMS, AND PE) PRECURSOR {C-TERMINAL}

[HUMAN, SALIVARY, PEPTIDE PARTIALMUTANT, 358 AA] [HOMO SAPIENS]

Matching:GPPPQGGNRPQGPPPP (Residues 91-96) (SEQ ID NO: 312)

GPPQQGGNRPQGPPPP (Residues 213-218) (SEQ ID NO: 313)

gi|433012|gb|AAB27291.1| (S62936) PRB1S PRECURSOR PROTEIN = BASIC

PROLINE-RICH PROTEINS (PS, PMF, PMS, AND PE) PRECURSOR {C-TERMINAL}

[HUMAN, SALIVARY, PEPTIDE PARTIALMUTANT, 236 AA] [HOMO SAPIENS]

Matching:GPPPQGGNRPQGPPPP (Residues 91-96) (SEQ ID NO: 314)

gi|539667|pir||D40750 PROLINE-RICH PROTEIN PRB1/2S (EA) - HUMAN (FRAGMENT) Matching:GPPPQGGNRPQGPPPP (Residues 91-96) (SEQ ID NO: 315)

gi|2144910|pir||PIHUB6 SALIVARY PROLINE-RICH PROTEIN PRECURSOR PRB1

(LARGE ALLELE) - HUMAN Matching:GPPQQGGNRPQGPPPP (Residues 247-

TABLE 6-continued

Sequence (formula) of the repetitive octapeptide motif GGNaP (SEQ ID NO: 15) of the salivary proteins is defined by shifting the formula GKPQβPPP (Table 3) in the sliding block window of the protein sequence for 14 amino acid residues left until the next residue Q, so that the structural formula GPPPPGKP is defined by means of the left and right residue Q, e.g. QGPPPPGKPQ. This procedure has been tested on a large set of salivary proteins in the nr Database of human protein sequences, by means of the software SCAN (3-5). The sequence is patented under the name SALIVAN.

252) (SEQ ID NO: 316)

gi|86621|pir||JH0481 BASIC PROLINE-RICH PROTEIN MNP4 - CRAB-EATING

MACAQUE Matching:GQPQQGGNRPQGPPSP (Residues 43-48) (SEQ ID NO: 317)

gi|266347|sp|P29681|IMP2_DROME 20-HYDROXYECDYSONE PROTEIN PRECURSOR (20-HE) Matching:IINFLGGNRPQNAPAA (Residues 375-380) (SEQ ID NO: 318)

gi|7300282|gb|AAF55444.1| (AE003718) CG14326 GENE PRODUCT

[DROSOPHILA MELANOGASTER] Matching:LGGLLGGNRPQPQPYP (Residues 77-82) (SEQ ID NO: 319)

gi|4582086|emb|CAB40256.1| (AJ241213) NADH DEHYDROGENASE SUBUNIT 1

[ECHINOCOCCUS GRANULOSUS] Matching:GGXXXQSFADL (Residues 1-6) (SEQ ID NO: 320)

TABLE 7

Decapeptide TAAPPTPSAT (SEQ ID NO: 18) is defined by means of the software SCAN (3-5) as the repetitive part of the salivary mucin (Mucin 7 precursor) and patented under the name MUCOSEPT.

| Repetitive sequence | Residue in the salivary Mucin 7 precursor |
|---|---|
| TAAPPTPSAT (SEQ ID NO: 18) | 166-175, 189-198, 235-244, 281-290 |

TABLE 8

Repetitive septapeptide motif PROCOL α of the sequence ADDANVV (SEQ ID NO: 19) was defined on the human proteins of the nr Database, by means of the software SCAN (3-5), in different type I collagen (α1 chain) structures.

| No. | Sequence ADDANVV (SEQ ID NO: 19) | Residue |
|---|---|---|
| 1 | Type I collagen, α1 chain propeptide | 40-46 |
| 2 | α1 chain propeptide | 794-800 |
| 3 | Pro α1 (I) collagen | 1215-1221 |
| 4 | Collagen α1 (I) chain precursor | 1218-1224 |
| 5 | Collagen, type I, α1 | 1218-1224 |

TABLE 9

General and specific variants of the repetitive septapeptide motif formula PROCOL α, with sequence ADDANVV (SEQ ID NO: 19) (Table 8).

| No. | General sequence | Specific sequence | Protein homology | Residue |
|---|---|---|---|---|
| 1 | aDAabb (SEQ ID NO: 20) | EDAGLV (SEQ ID NO: 21) | Telomeric repeat binding factor 1 | 62-67 |

TABLE 9-continued

General and specific variants of the repetitive septapeptide motif formula PROCOL α, with sequence ADDANVV (SEQ ID NO: 19) (Table 8).

| No. | General sequence | Specific sequence | Protein homology | Residue |
|---|---|---|---|---|
| 2 | AaDAabb (SEQ ID NO: 22) | AKDAGLV (SEQ ID NO: 23) | Multidrug resistance gene MRP1 | 395-401, 1394-1400, 1444-1450, 1450-1456, 1453-1459, 1509-1515, 1525-1531 |
| 3 | AaDAabb (SEQ ID NO: 22) | AKDAGLV (SEQ ID NO: 23) | ATP-binding cassette, sub-family C | 1525-1531 |
| 4 | ADDAbabbb (SEQ ID NO: 24) | ADDAMTLVL (SEQ ID NO: 25) | Endoglin precursor | 351-359 |
| 5 | ADDAbabbb (SEQ ID NO: 24) | ADDAMTLVL (SEQ ID NO: 25) | Endoglin precursor (CD105 antigen) | 364-372 |
| 6 | bbaaAAabb (SEQ ID NO: 26) | VHPRAAGLV (SEQ ID NO: 27) | Bone morphogenetic protein 6 precursor | 339-347 | a = polar amino acid (N, D, E, Q, P, R, S, K, T, G or A),
b = non-polar amino acid (V, L, M, W, I, F, C, H or Y), as defined in FIG. 1.

FIG. 1. Division of 20 amino acids into the two groups (polar and non-polar ones), was performed by means of the statistical clustering procedure of "partitioning around medoids", on the standard hydropathy scale of Rose et al. (10). We used parameter f of the scale, that measures "the mean frictional area loss of the amino acid residue within the protein molecule". The analysis was done by means of the software package S-Plus, with standard pam method (11). The values of Silhouette plot presented in the figure confirm statistically significant clustering of the 20 amino acid set into the two groups of the amino acids, a and b (11). Group a of polar amino acids consists of the N, D, E, Q, P, R, S, K, T, G and A while group b of non-polar amino acids consists of the amino acids V, L, M, W, I, F, C, H and Y.

The invention claimed is:

1. A pharmaceutical composition comprising at least one polypeptide, wherein the polypeptide consists of SEQ ID NO: 5 and the amino acid at the first position of SEQ ID NO: 5 is selected from the group consisting of asparagine, aspartate, glutamate, glutamine, arginine, serine, lysine, threonine, or alanine.

2. The pharmaceutical composition of claim 1, further comprising a second polypeptide.

3. The pharmaceutical composition of claim 2, wherein the second polypeptide comprises SEQ ID NO: 2.

4. The pharmaceutical composition of claim 3, wherein the second polypeptide comprises SEQ ID NO: 1.

5. The pharmaceutical composition of claim 3, wherein the second polypeptide consists of SEQ ID NO: 1.

6. The pharmaceutical composition of claim 3, wherein the second polypeptide comprises any of SEQ ID NO: 28 to 194.

7. The pharmaceutical composition of claim 2, wherein the second polypeptide comprises SEQ ID NO: 15.

8. The pharmaceutical composition of claim 7, wherein the second polypeptide comprises SEQ ID NO: 16.

9. The pharmaceutical composition of claim 7, wherein the second polypeptide consists of SEQ ID NO: 16.

10. The pharmaceutical composition of claim 7, wherein the second polypeptide comprises any of SEQ ID NO: 253 to 320.

11. The pharmaceutical composition of claim 1, wherein the pharmaceutical composition is suitable for topical administration.

12. The pharmaceutical composition of claim 11, wherein the pharmaceutical composition is formulated as an ointment, cream, gel, drops or suppository.

13. The pharmaceutical composition of claim 1, wherein the pharmaceutical composition is suitable for systemic administration.

14. The pharmaceutical composition of claim 13, wherein the systemic administration is selected from the group consisting of oral, subcutaneous, rectal, inhalation, intramuscular, intraperitoneal and intravenous administration.

* * * * *

```
                        SEQUENCE LISTING

<160> NUMBER OF SEQ ID NOS: 27

<210> SEQ ID NO 1
<211> LENGTH: 8
<212> TYPE: PRT
<213> ORGANISM: Artificial Sequence
<220> FEATURE:
<223> OTHER INFORMATION: Artificial amino acid sequence SALIVAR which
      is common and repetitive building block of a large number of
      salivary proline rich proteins.

<400> SEQUENCE: 1

Gly Lys Pro Gln Gly Pro Pro Pro
1               5

<210> SEQ ID NO 2
<211> LENGTH: 8
<212> TYPE: PRT
<213> ORGANISM: Artificial Sequence
<220> FEATURE:
<223> OTHER INFORMATION: Artificial amino acid sequence SALIVAR which
      is common and repetitive building block of a large number of
      salivary proline rich proteins. Glx defines amino acids Gln and
      Glu. Xaa defines amino acids: Gly, Arg and Glu.

<400> SEQUENCE: 2

Gly Lys Pro Glx Xaa Pro Pro Pro
1               5

<210> SEQ ID NO 3
<211> LENGTH: 8
<212> TYPE: PRT
<213> ORGANISM: Artificial Sequence
<220> FEATURE:
<223> OTHER INFORMATION: Artificial amino acid sequence SALIVAL which
      is common and repetitive building block of a large number of
      salivary proline rich proteins.

<400> SEQUENCE: 3

Gly Pro Pro Pro Pro Gly Lys Pro
1               5

<210> SEQ ID NO 4
<211> LENGTH: 7
<212> TYPE: PRT
<213> ORGANISM: Artificial Sequence
<220> FEATURE:
<223> OTHER INFORMATION: Artificial amino acid sequence SALIVAL which
      is common and repetitive building block of a large number of
      salivary proline rich proteins. In this artificial sequence
      variant Xaa defines amino acids: Val, Leu, Met, Trp, Ile, Phe,
      Cys, His and Tyr.

<400> SEQUENCE: 4

Xaa Pro Pro Pro Pro Gly Lys
1               5

<210> SEQ ID NO 5
<211> LENGTH: 7
<212> TYPE: PRT
<213> ORGANISM: Artificial Sequence
<220> FEATURE:
```

-continued

```
<223> OTHER INFORMATION: Artificial amino acid sequence SALIVAL which
      is common and repetitive building block of a large number of
      salivary proline rich proteins. In this artificial sequence
      variant Xaa defines amino acids: Asn, Asp, Glu, Gln, Pro, Arg,
      Ser, Lys, Thr, Gly and Ala.

<400> SEQUENCE: 5

Xaa Pro Pro Pro Pro Gly Lys
 1               5

<210> SEQ ID NO 6
<211> LENGTH: 7
<212> TYPE: PRT
<213> ORGANISM: Artificial Sequence
<220> FEATURE:
<223> OTHER INFORMATION: Artificial amino acid sequence SALIVAL which
      is common and repetitive building block of a large number of
      salivary proline rich proteins. In this artificial sequence
      variant Xaa defines amino acids: Val, Leu, Met, Trp, Ile, Phe,
      Cys, His and Tyr.

<400> SEQUENCE: 6

Pro Pro Pro Pro Gly Lys Xaa
 1               5

<210> SEQ ID NO 7
<211> LENGTH: 7
<212> TYPE: PRT
<213> ORGANISM: Artificial Sequence
<220> FEATURE:
<223> OTHER INFORMATION: Artificial amino acid sequence SALIVAL which
      is common and repetitive building block of a large number of
      salivary proline rich proteins. In this artificial sequence
      variant Xaa defines amino acids: Asn, Asp, Glu, Gln, Pro, Arg,
      Ser, Lys, Thr, Gly and Ala.

<400> SEQUENCE: 7

Pro Pro Pro Pro Gly Lys Xaa
 1               5

<210> SEQ ID NO 8
<211> LENGTH: 8
<212> TYPE: PRT
<213> ORGANISM: Artificial Sequence
<220> FEATURE:
<223> OTHER INFORMATION: Artificial amino acid sequence SALIVAL which
      is common and repetitive building block of a large number of
      salivary proline rich proteins. In this artificial sequence
      variant Xaa defines amino acids: Val, Leu, Met, Trp, Ile, Phe,
      Cys, His and Tyr.

<400> SEQUENCE: 8

Xaa Pro Pro Pro Pro Gly Lys Xaa
 1               5

<210> SEQ ID NO 9
<211> LENGTH: 8
<212> TYPE: PRT
<213> ORGANISM: Artificial Sequence
<220> FEATURE:
<223> OTHER INFORMATION: Artificial amino acid sequence SALIVAL which
      is common and repetitive building block of a large number of
      salivary proline rich proteins. In this artificial sequence
      variant the first residue (No. 1) Xaa defines amino acids: Val,
      Leu, Met, Trp, Ile, Phe, Cys, His and Tyr. The last
      residue (No. 8) Xaa defines amino acids: Asn, Asp, Glu,
      Gln, Pro, Arg, Ser, Lys, Thr, Gly and Ala.

<400> SEQUENCE: 9

Xaa Pro Pro Pro Pro Gly Lys Xaa
```

-continued

<210> SEQ ID NO 10
<211> LENGTH: 8
<212> TYPE: PRT
<213> ORGANISM: Artificial Sequence
<220> FEATURE:
<223> OTHER INFORMATION: Artificial amino acid sequence SALIVAL which
      is common and repetitive building block of a large number of
      salivary proline rich proteins. In this artificial sequence
      variant the first residue (No. 1) Xaa defines amino acids: Asn,
      Asp, Glu, Gln, Pro, Arg, Ser, Lys, Thr, Gly and Ala.
      The last residue (No. 8) Xaa defines amino acids: Val,
      Leu, Met, Trp, Ile, Phe, Cys, His and Tyr.

<400> SEQUENCE: 10

Xaa Pro Pro Pro Pro Gly Lys Xaa
 1               5

<210> SEQ ID NO 11
<211> LENGTH: 8
<212> TYPE: PRT
<213> ORGANISM: Artificial Sequence
<220> FEATURE:
<223> OTHER INFORMATION: Artificial amino acid sequence SALIVAL which
      is common and repetitive building block of a large number of
      salivary proline rich proteins. In this artificial sequence
      variant Xaa defines amino acids: Asn, Asp, Glu, Gln,
      Pro, Arg, Ser, Lys, Thr, Gly and Ala.

<400> SEQUENCE: 11

Xaa Pro Pro Pro Pro Gly Lys Xaa
 1               5

<210> SEQ ID NO 12
<211> LENGTH: 8
<212> TYPE: PRT
<213> ORGANISM: Artificial Sequence
<220> FEATURE:
<223> OTHER INFORMATION: Artificial amino acid sequence SALIVAL which
      is common and repetitive building block of a large number of
      salivary proline rich proteins. In this artificial sequence
      variant Xaa defines amino acids: Asn, Asp, Glu, Gln, Pro, Arg,
      Ser, Lys, Thr, Gly and Ala.

<400> SEQUENCE: 12

Xaa Xaa Pro Pro Pro Gly Xaa Xaa
 1               5

<210> SEQ ID NO 13
<211> LENGTH: 7
<212> TYPE: PRT
<213> ORGANISM: Artificial Sequence
<220> FEATURE:
<223> OTHER INFORMATION: Artificial amino acid sequence SALIVAL. This
      specific variant has sequence homology to the short
      region (residues 865-871) of the Telomerase associated protein 1.

<400> SEQUENCE: 13

Ile Pro Pro Pro Pro Gly Lys
 1               5

<210> SEQ ID NO 14
<211> LENGTH: 8
<212> TYPE: PRT
<213> ORGANISM: Artificial Sequence
<220> FEATURE:
<223> OTHER INFORMATION: Artificial amino acid sequence SALIVAL. This
      specific variant has sequence homology to the short
      region (residues 122-129) of the Bone morphogenetic protein 6 precursor.

<400> SEQUENCE: 14

Gly Glu Pro Pro Gly Lys Pro
1               5

<210> SEQ ID NO 15
<211> LENGTH: 5
<212> TYPE: PRT
<213> ORGANISM: Artificial Sequence
<220> FEATURE:
<223> OTHER INFORMATION: Artificial amino acid sequence SALIVAN which
      is common and repetitive building block of a large number of
      salivary proline rich proteins. In this artificial sequence
      variant Xaa defines amino acids: Asn, Asp, Glu, Gln, Pro, Arg,
      Ser, Lys, Thr, Gly and Ala.

<400> SEQUENCE: 15

Gly Gly Asn Xaa Pro
1               5

<210> SEQ ID NO 16
<211> LENGTH: 5
<212> TYPE: PRT
<213> ORGANISM: Artificial Sequence
<220> FEATURE:
<223> OTHER INFORMATION: Artificial amino acid sequence SALIVAN which
      is common and repetitive building block of a large number of
      salivary proline rich proteins.

<400> SEQUENCE: 16

Gly Gly Asn Lys Pro
1               5

<210> SEQ ID NO 17
<211> LENGTH: 5
<212> TYPE: PRT
<213> ORGANISM: Artificial Sequence
<220> FEATURE:
<223> OTHER INFORMATION: Artificial amino acid sequence SALIVAN which
      is common and repetitive building block of a large number of
      salivary proline rich proteins.

<400> SEQUENCE: 17

Gly Gly Asn Arg Pro
1               5

<210> SEQ ID NO 18
<211> LENGTH: 10
<212> TYPE: PRT
<213> ORGANISM: Artificial Sequence
<220> FEATURE:
<223> OTHER INFORMATION: Artificial amino acid sequence MUCOSEPT which
      is repetitive part of the salivary mucin (Mucin 7 precursor).

<400> SEQUENCE: 18

Thr Ala Ala Pro Pro Thr Pro Ser Ala Thr
1               5                   10

<210> SEQ ID NO 19
<211> LENGTH: 7
<212> TYPE: PRT
<213> ORGANISM: Artificial Sequence
<220> FEATURE:
<223> OTHER INFORMATION: Artificial amino acid sequence PROCOL alpha
      which is repetitive part of human type I collagen (alpha 1 chain)
      structures.

<400> SEQUENCE: 19

```
Ala Asp Asp Ala Asn Val Val
  1               5

<210> SEQ ID NO 20
<211> LENGTH: 6
<212> TYPE: PRT
<213> ORGANISM: Artificial Sequence
<220> FEATURE:
<223> OTHER INFORMATION: Artificial amino acid sequence PROCOL alpha.
      In this artificial sequence variant the first and fourth residue
      Xaa (No. 1 & 4 ) define amino acids: Asn, Asp, Glu, Gln, Pro,
      Arg, Ser, Lys, Thr, Gly and Ala. The fifth and sixth sequence
      residue Xaa (No. 5 & 6) define amino acids: Val, Leu, Met, Trp,
      Ile, Phe, Cys, His and Tyr.

<400> SEQUENCE: 20

Xaa Asp Ala Xaa Xaa Xaa
  1               5

<210> SEQ ID NO 21
<211> LENGTH: 6
<212> TYPE: PRT
<213> ORGANISM: Artificial Sequence
<220> FEATURE:
<223> OTHER INFORMATION: Artificial amino acid sequence PROCOL alpha.
      This specific variant has sequence homology to the short
      region (residues 62-67) of the Telomeric repeat binding factor 1.

<400> SEQUENCE: 21

Glu Asp Ala Gly Leu Val
  1               5

<210> SEQ ID NO 22
<211> LENGTH: 7
<212> TYPE: PRT
<213> ORGANISM: Artificial Sequence
<220> FEATURE:
<223> OTHER INFORMATION: Artificial amino acid sequence PROCOL alpha.
      In this artificial sequence variant the second and fifth residue
      Xaa (No. 2 & 5 ) define amino acids: Asn, Asp, Glu, Gln, Pro,
      Arg, Ser, Lys, Thr, Gly and Ala. The sixth and seventh sequence
      residue Xaa (No. 6 & 7) define amino acids: Val, Leu, Met, Trp,
      Ile, Phe, Cys, His and Tyr.

<400> SEQUENCE: 22

Ala Xaa Asp Ala Xaa Xaa Xaa
  1               5

<210> SEQ ID NO 23
<211> LENGTH: 7
<212> TYPE: PRT
<213> ORGANISM: Artificial Sequence
<220> FEATURE:
<223> OTHER INFORMATION: Artificial amino acid sequence PROCOL alpha.
      This specific variant has sequence homology to the short
      regions of the Multidrug resistance gene MRP1 and
      ATP-binding cassette, sub-family C.

<400> SEQUENCE: 23

Ala Lys Asp Ala Gly Leu Val
  1               5

<210> SEQ ID NO 24
<211> LENGTH: 9
<212> TYPE: PRT
<213> ORGANISM: Artificial Sequence
<220> FEATURE:
<223> OTHER INFORMATION: Artificial amino acid sequence PROCOL alpha.
      In this artificial sequence variant the fifth, seventh, eighth
```

-continued

```
       and ninth residue Xaa (No. 5, 7, 8 & 9 ) define amino acids:
       Val, Leu, Met, Trp, Ile, Phe, Cys, His and Tyr. The sixth
       sequence residue Xaa (No. 6) defines amino acids: Asn, Asp, Glu,
       Gln, Pro, Arg, Ser, Lys, Thr, Gly and Ala.

<400> SEQUENCE: 24

Ala Asp Asp Ala Xaa Xaa Xaa Xaa Xaa
 1               5

<210> SEQ ID NO 25
<211> LENGTH: 9
<212> TYPE: PRT
<213> ORGANISM: Artificial Sequence
<220> FEATURE:
<223> OTHER INFORMATION: Artificial amino acid sequence PROCOL alpha.
       This specific variant has sequence homology to the short
       regions of the Endoglin precursor, CD105 antigen.

<400> SEQUENCE: 25

Ala Asp Asp Ala Met Thr Leu Val Leu
 1               5

<210> SEQ ID NO 26
<211> LENGTH: 9
<212> TYPE: PRT
<213> ORGANISM: Artificial Sequence
<220> FEATURE:
<223> OTHER INFORMATION: Artificial amino acid sequence PROCOL alpha.
       In this artificial sequence variant the first, second, eighth
       and ninth residue Xaa (No. 1, 2, 8 & 9 ) define amino acids:
       Val, Leu, Met, Trp, Ile, Phe, Cys, His and Tyr. The third, fourth
       and seventh sequence residue Xaa (No. 3, 4 & 7) define amino
       acids: Asn, Asp, Glu, Gln, Pro, Arg, Ser, Lys, Thr, Gly and Ala.

<400> SEQUENCE: 26

Xaa Xaa Xaa Xaa Ala Ala Xaa Xaa Xaa
 1               5

<210> SEQ ID NO 27
<211> LENGTH: 9
<212> TYPE: PRT
<213> ORGANISM: Artificial Sequence
<220> FEATURE:
<223> OTHER INFORMATION: Artificial amino acid sequence PROCOL alpha.
       This specific variant has sequence homology to the short
       region of the Bone morphogenetic protein 6 precursor.

<400> SEQUENCE: 27

Val His Pro Arg Ala Ala Gly Leu Val
 1               5
```